(12) United States Patent
Kim et al.

(10) Patent No.: US 12,005,108 B2
(45) Date of Patent: Jun. 11, 2024

(54) LACTOCOCCUS LACTIS SUBSPECIES LACTIS ISOLATE WFLU-12 AND USE THEREOF

(71) Applicant: PUKYONG NATIONAL UNIVERSITY INDUSTRY-UNIVERSITY COOPERATION FOUNDATION, Busan (KR)

(72) Inventors: Do-Hyung Kim, Busan (KR); Thanh Luan Nguyen, Busan (KR); Nam-Eun Kim, Busan (KR)

(73) Assignee: PUKYONG NATIONAL UNIVERSITY INDUSTRY-UNIVERSITY COOPERATION FOUNDATION, Busan (KR)

( * ) Notice: Subject to any disclaimer, the term of this patent is extended or adjusted under 35 U.S.C. 154(b) by 0 days.

(21) Appl. No.: 17/643,942

(22) Filed: Dec. 13, 2021

(65) Prior Publication Data
US 2023/0235276 A1 Jul. 27, 2023

Related U.S. Application Data

(63) Continuation of application No. 16/652,373, filed as application No. PCT/KR2017/001615 on Feb. 14, 2017, now abandoned.

(51) Int. Cl.
| | | |
|---|---|---|
| *A61K 35/744* | (2015.01) |
| *A23K 10/18* | (2016.01) |
| *A23K 50/80* | (2016.01) |
| *A61K 39/02* | (2006.01) |
| *A61K 39/09* | (2006.01) |
| *C12N 1/20* | (2006.01) |
| *A61K 39/106* | (2006.01) |

(52) U.S. Cl.
CPC .......... *A61K 39/092* (2013.01); *A23K 10/18* (2016.05); *A23K 50/80* (2016.05); *A61K 35/744* (2013.01); *A61K 39/025* (2013.01); *A61K 39/09* (2013.01); *C12N 1/20* (2013.01); *A23V 2400/231* (2023.08); *A61K 2039/106* (2013.01)

(58) Field of Classification Search
None
See application file for complete search history.

(56) References Cited

FOREIGN PATENT DOCUMENTS

| | | |
|---|---|---|
| JP | 2006-265181 A | 10/2006 |
| KR | 10-2009-0035960 A | 4/2009 |
| KR | 10-2014-0090854 A | 7/2014 |

OTHER PUBLICATIONS

Thanh Luan Nguyen et al., "Improved growth rate and disease resistance in olive flounder, Paralichthys olivaceus, by probiotic Lactococcus lactis WFLU12 isolated from wild marine fish", Aqculture, www.elsevier.com/locate/aquaculture, Jan. 9, 2017, V. 471, p. 113-120, Republic of Korea.
Won-Seok Heo et al., "Effects of dietary probiotic, Lactococcus lactis subsp. lactis 12, supplementation on the growth and immune response of oliver flounder (Paralichthys olivaceus)", Aquaculture, www.elsevier.com/locate/aqua-online, Nov. 16, 2012, V. 376-379, p. 20-24, Republic of Korea.
"Lactococcus lactis subsp. lactis strain: WFLU12," NCBr, BioProject accession No. PRJNA338902, Aug. 15, 2016.
International Preliminary Report on Patentability from corresponding PCT Application No. PCT/KR2017/001615, dated Jul. 23, 2019.
International Search Report from corresponding PCT Application No. PCT/KR2017/001615, dated Oct. 24, 2017.
Non-Final Office Action dated May 11, 2021 in U.S. Appl. No. 16/652,373.

*Primary Examiner* — S. Devi
(74) *Attorney, Agent, or Firm* — Harness, Dickey & Pierce, P.L.C.

(57) ABSTRACT

The present invention provides a *Lactococcus lactis* subspecies *lactis* isolate WFLU-12 with the accession number o KCTC 13180BP, and a use thereof.

7 Claims, 17 Drawing Sheets

LACTOCOCCUS LACTIS SUBSPECIES LACTIS ISOLATE WFLU-12 AND USE THEREOF

CROSS-REFERENCE TO RELATED APPLICATIONS

This application is a continuation of U.S. patent application Ser. No. 16/652,373, filed on 30 Mar. 2020 (now abandoned), which is a national phase application of PCT Application No. PCT/KR2017/001615, filed on 14 Feb. 2017, which claims priority to Korean Patent Application No. 10-2017-0010635, filed on 23 Jan. 2017. The entire disclosure of the applications identified in this paragraph is incorporated herein by reference.

TECHNICAL FIELD

The present invention relates to a novel *Lactococcus lactis* subspecies *lactis* isolate WFLU-12, and a use thereof.

BACKGROUND ART

The world fish food aquaculture production in 2012 was recorded as 44.2 million tons of fish (66%), 15.2 million tons of mollusks (23%), 6.4 million tons of crustaceans (10%), and 0.9 million tons of other species (1%). The inland aquaculture production was 38.6 million tons, which accounts for 58% of the world total aquaculture production in 2012. The proportion of aquaculture in the total fish production is steadily on an increase around the world. In Asia, the fish production of aquaculture exceeded the fish production of the general fishing industry (capture) since 2008, and the fish production of aquaculture accounted for 54% of the total fish production in 2012. This is a remarkably high figure compared to 18% in Europe and less than 15% in other countries, and aquaculture accounts for a very high share in the food industry of Asia (FAO yearbook, Fishery and Aquaculture Statistics. 2012). For fish aquaculture, high quality feed is important, and feed in this regard is a concept including not only essential nutrients but also supplementary feed additives. The feed affects the health, growth and development of the fish body, and should be eco-friendly.

Feed additives are defined as substances added to the feed in trace amounts, affecting not only the nutrition and growth rate but also the health of the fish body. Most feed additives used to promote growth include hormones, antibiotics, ionospheres, and some salts. Probiotics use living microorganisms among these feed additives to improve the intestinal microbial balance in the host and promote the growth of the host. For aquaculture, probiotics have been evaluated in terms of pathogen suppression, water quality improvement, immune response activity of host, promotion of nutritional absorption through the production of additional digestive enzymes, etc. (Verschuere et al., 2002; Carnevali et al., 2006). For such reasons, the use of probiotics is drawing attention in fish aquaculture around the world. Representative probiotic strains commonly used include *Lactobacillus acidophilus, L. bulgaricus, L. plantariu, Lactococcus lactis, Saccharomyces cerevisiae* (FAO, 2004).

The most significant benefit of using probiotics as a feed additive is that probiotics may be used as a substitute for antibiotics. At the moment, fish aquaculture depends on the use of antibiotics and chemotherapeutics in order to control and prevent bacterial diseases. However, the use of antibiotics and chemotherapeutics may cause selective pressure, thereby creating antibiotic resistant bacteria in the aquatic environment, increasing antibiotic tolerance in fish pathogens, and subsequently delivering tolerance determinants which exist in bacteria and fish pathogens to the pathogens of land animals and humans. Therefore, it is imminent to develop a substance which can replace antibiotics and chemotherapeutics for fish aquaculture. In this aspect, probiotics are the most suitable substitute capable of eliminating the risk of creating antibiotic resistant bacteria. In many researches, the use of probiotics has been proved to be effective in decreasing disease infection and mortality due to the host immune activity and direct pathogen suppression, making it an eco-friendly aquaculture technology.

In Korea, the rapid expansion of the aquaculture industry has been severely impacted by bacterial pathogens. Specifically, the loss caused by *Streptococcus* iniae and *S. parauberis*, which are the major pathogens of streptococcal diseases in flounder, accounted for the greatest portion. A long-term use of antibiotics for controlling streptococcal diseases in flounder contributed to a higher rate of antibiotic tolerance in *S. parauberis* than in *S. iniae* (Park et al., 2009). Therefore, as an alternative, it may be considered to reduce the use of antibiotics and use proper probiotics to prevent the propagation of tolerance in *S. parauberis*.

In light of the above, as a result of conducting continuous research on a probiotic isolate which has not only an excellent antibacterial activity against pathogens and excellent effect in preventing infection, but also an excellent effect in promoting the growth of fish body, and a feed additive comprising the same, the inventors of the present invention completed the present invention.

DETAILED DESCRIPTION

Technical Task

The present invention aims to provide an isolate with an excellent antibacterial activity against pathogens which is used in a probiotic composition to enhance innate immune response of fish and promote the growth of fish body.

Also, the present invention aims to provide a probiotic composition, an antibacterial composition, and a feed additive and a feed for fish farming, comprising the isolate.

Also, the present invention aims to provide a method of promoting the growth of farmed fish and a method of preventing infection by pathogens of farmed fish, using the isolate.

Means for Solving Task

An embodiment of the present invention provides a *Lactococcus lactis* subspecies *lactis* isolate WFLU-12 with the accession number KCTC13180BP.

The isolate may show resistance to a temperature of at least 4° C., preferably a temperature of 4-10° C., a pH of 2-10, and a bile acid.

Also, the isolate may have an antibacterial activity against at least one selected from the group consisting of a Gram-negative bacterium of *Vibrio anguillarum, V. ichthyoenteri, Aeromonas salmonicida, Edwardsiella tarda, Photobacterium damselae* or a Gram-positive bacterium of *Streptococcus iniae, S. parauberis.*

Another embodiment of the present invention provides a probiotic composition comprising the isolate, a culture thereof, a lysate thereof or an extract thereof as an active ingredient.

The probiotic composition may present at least one effect selected from enhancing innate immune response of fish, increasing body weight, increasing body length, enhancing body circulating metabolite, maintaining homeostasis of metabolite, increasing sulfur-containing amino acid level in body, increasing taurine level in intestine, enhancing citrulline level in body, and enhancing vitamin level in intestine.

Another embodiment of the present invention provides an antibacterial composition comprising the isolate, a culture thereof, a lysate thereof or an extract thereof as an active ingredient.

Another embodiment of the present invention provides a feed additive for fish farming, comprising the probiotic composition or the antibacterial composition as an active ingredient.

Another embodiment of the present invention provides a feed for fish farming, comprising the feed additive.

Another embodiment of the present invention provides a method of promoting the growth of farmed fish, comprising feeding the feed to the fish being farmed.

Another embodiment of the present invention provides a method of preventing infection by pathogens of farmed fish, comprising spraying the antibacterial composition to a fish farm.

Effect of Invention

The novel *Lactococcus lactis* subspecies *lactis* isolate WFLU-12 of the present invention has excellent storage stability and antibacterial activity against pathogens, and the probiotic composition comprising the same presents effects of enhancing innate immune response of fish and promoting the growth of fish body. Therefore, it would be possible to improve the profits of the aquaculture industry by using a probiotic composition, an antibacterial composition, and a feed additive and a feed for fish farming, comprising the isolate.

BEST MODE FOR CARRYING OUT THE INVENTION

An embodiment of the present invention provides a *Lactococcus lactis* subspecies *lactis* isolate WFLU-12 with the accession number KCTC13180BP. The *Lactococcus lactis* subspecies *lactis* isolate WFLU-12 of the present invention was isolated from a gastrointestinal tract of a flounder. The 16S rRNA gene sequence analysis showed a homology of 99.6%, and was identified as a *Lactococcus lactis* subspecies *lactis* type strain (RDP SEMATCH program). The API CH50 test results showed a homology of 99.9% to same species.

Figure 1A:
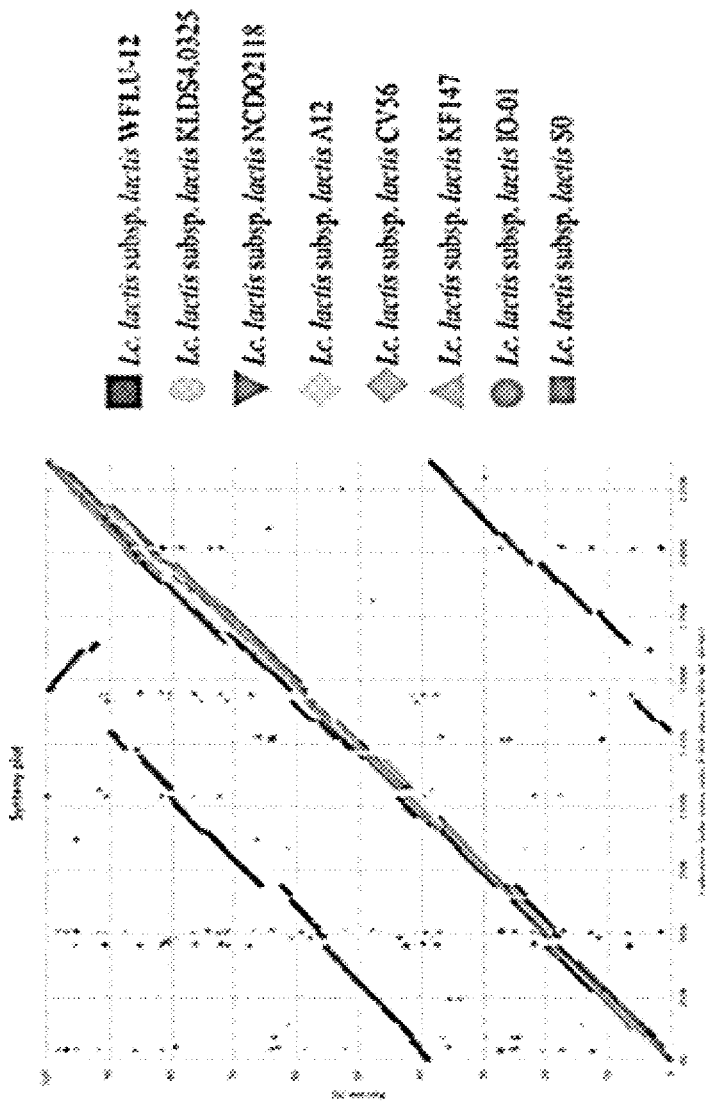
FIG. 1a to FIG. 1d illustrate the result of comparing the entire genomes between an isolate WFLU-12 and isolates from different orientations according to an embodiment of the present invention.
Figure 1B:
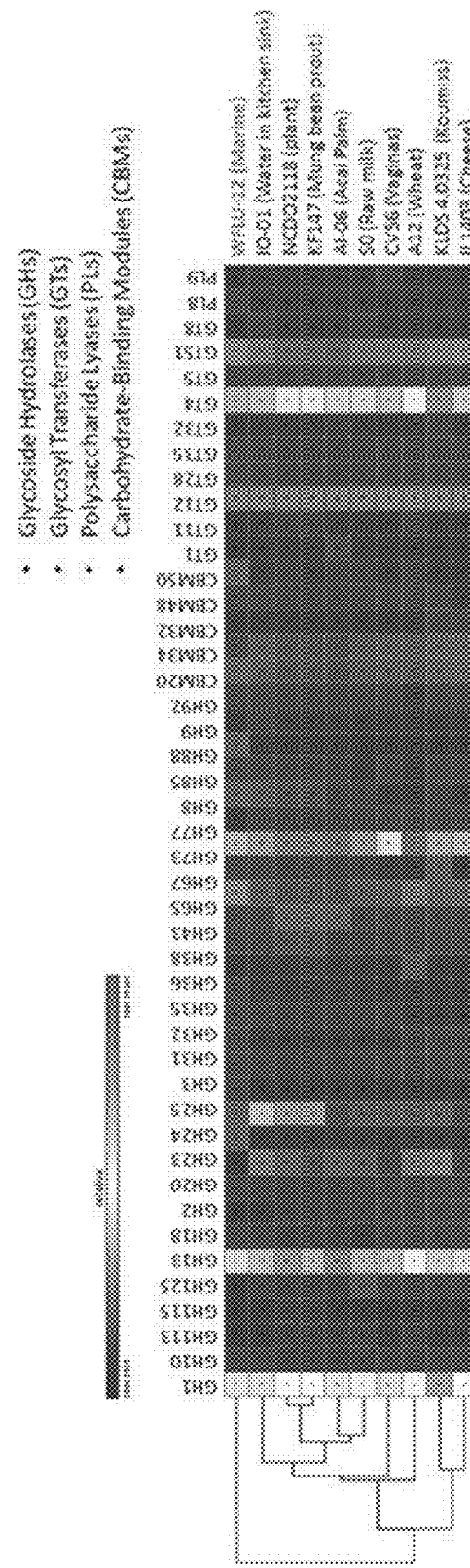
Figure 1C:
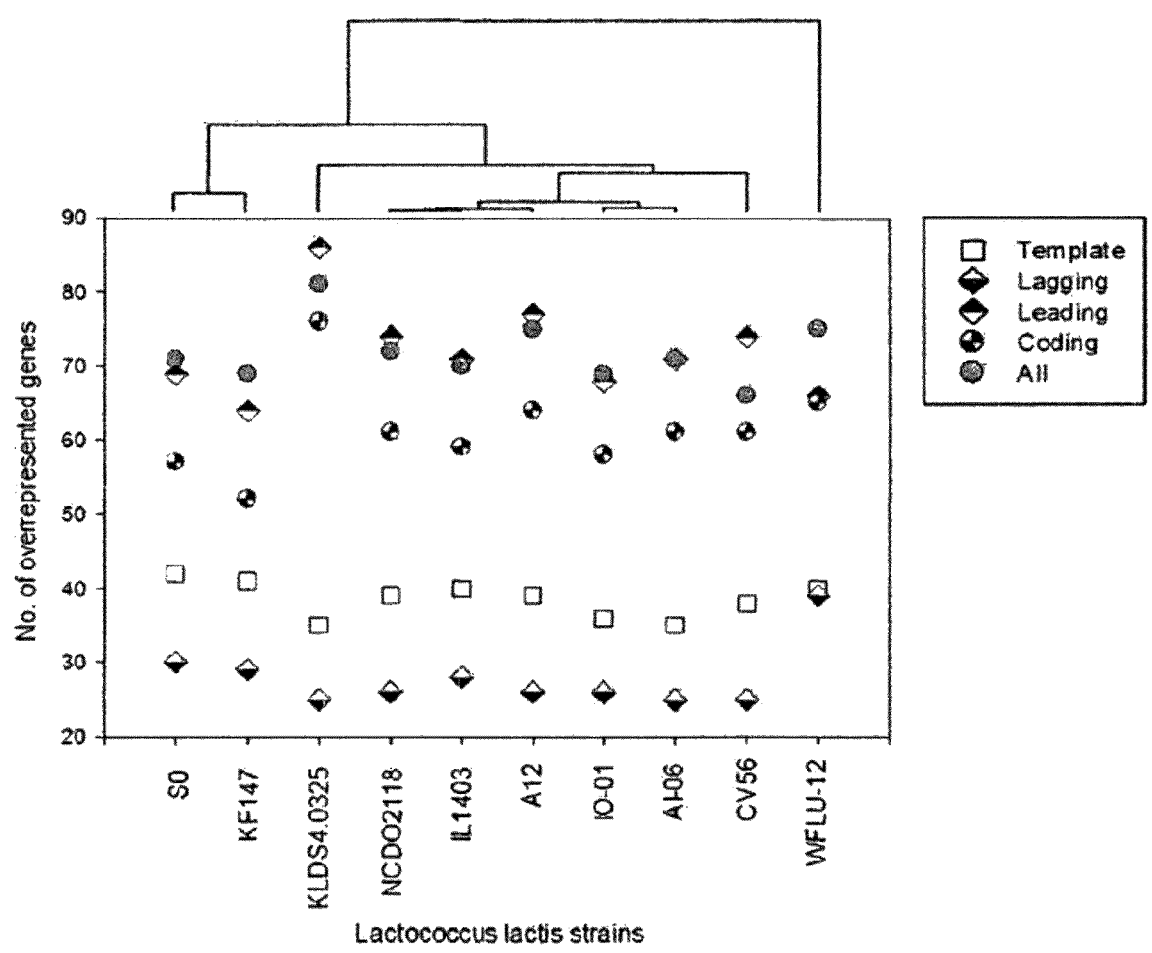
Figure 1D:
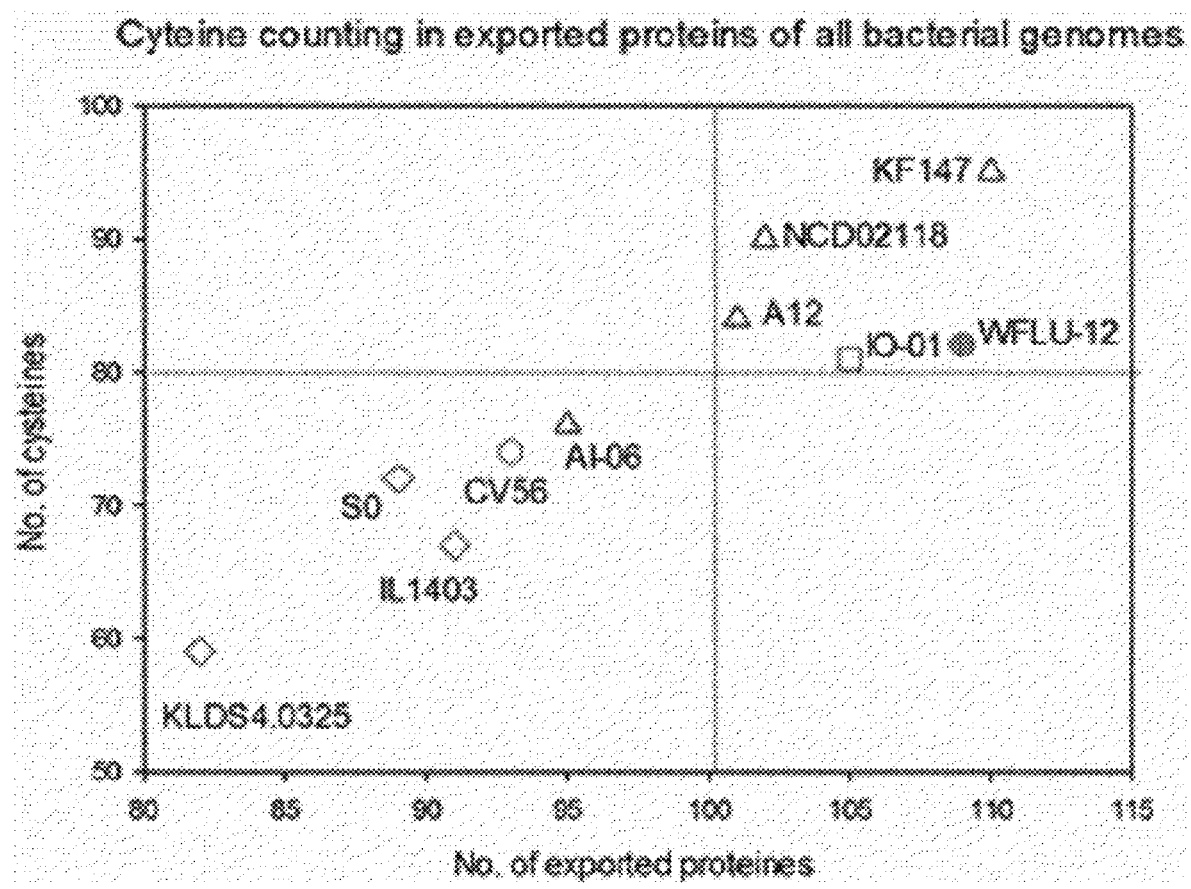

Comparative Analysis of the Entire Genomes Between Isolate WFLU-12 and Isolates from Different Orientations As a result of analyzing the synteny of the isolate WFLU-12 of the present invention and the isolates from different orientations, the isolate WFLU-12 of the present invention formed a distinctive synteny compared to the isolates from different orientations (FIG. 1a). Also, as a result of comparing the genomes between the isolate WFLU-12 and the isolates from different orientations, various specific features showing gene relocation and adaptation to the intestinal environment have been found. For example, features such as adhesion, stress resistance (cold shock resistance CspB, CspA, CspC, CspF, CspG), use of carbohydrate (CAZY profile) (FIG. 1b), and encoding gene clusters associated with bacteriocin (biosynthesis of antibiotic nisin Z and production of colicin V) have been found. Interestingly, as a result of annotation of these isolates, lysozyme (two genes), and singleton gene (specific gene) associated with the fimbrial gene cluster were found only in WFLU-12. In addition, a variety of genes including the overexpression of Chi site (DNA motif), which is confirmed to help maintain chromosomes, were found in WFLU-12 (FIG. 1c). FIG. 1c shows that both the isolate WFLU-12 and the isolates from different orientations presented high expression of Chi sites (DNA motifs). In addition, the number of transfer proteins and cysteine exclusion was higher in the isolate WFLU-12 (FIG. 1d).

Also, the inventors of the present invention found that the *Lactococcus lactis* subspecies *lactis* isolate WFLU-12 of the present invention with its good functional genes is distinguished from other isolates, has excellent resistance to a low temperature, various pH environments and bile acids and excellent storage stability, and has an excellent antibacterial activity against various fish pathogens, and completed the present invention.

Specifically, the isolate WFLU-12 of the present invention grows well at a temperature between 4° C. and room temperature and under pH conditions of 2-10, and in particular has good resistance to bile acids. Also, the isolate of the present invention may have an antibacterial activity against at least one selected from the group consisting of a Gram-negative bacterium of *Vibrio anguillarum, V. ichthyoenteri, Aeromonas salmonicida, Edwardsiella tarda, Photobacterium damselae* or a Gram-positive bacterium of *Streptococcus iniae, S. parauberis*.

The present inventors deposited the isolate WFLU-12 of the present invention at the Biological Resources Center of the Korean Collection for Type Cultures (KCTC), which is an international depositary institution under the Budapest Treaty, on Jan. 3, 2017, and received accession number KCTC13180BP.

According to another embodiment of the present invention, the present invention provides a probiotic composition comprising the isolate, a culture thereof, a lysate thereof or an extract thereof as an active ingredient.

The term "culture" in the present invention means the entire medium including cultured strains obtained by culturing the isolate for a certain period of time in a medium capable of supplying nutrients so that the isolate WFLU-12 of the present invention can grow and survive in vitro, metabolites thereof, and extra nutrients, etc., and also includes culture solutions in which strains are removed after culturing the strains.

The term "probiotic" in the present invention means living microorganisms, i.e., biomicrobial species beneficial to the health of intestinal flora, i.e., the health of the host. In general, probiotics are consumed as part of fermented food such as yogurt, etc. or as dietary supplements. Microorganisms known as probiotics include lactic acid bacteria (LAB), bifidobacteria, some yeasts and *bacillus*, etc.

In addition, the probiotic composition of the present invention may present at least one effect selected from enhancing innate immune response of fish, increasing body weight, increasing body length, enhancing body circulating metabolite, maintaining homeostasis of metabolite, increasing sulfur-containing amino acid level in body, increasing taurine level in intestine, enhancing citrulline level in body, and enhancing vitamin level in intestine.

According to another embodiment, the present invention provides an antibacterial composition comprising the isolate, a culture thereof, a lysate thereof or an extract thereof as an active ingredient. Since the isolate WFLU-12 has an antibacterial activity, particularly an antibacterial activity against fish bacterial pathogens, the isolate WFLU-12 or a culture thereof may be used as an antibacterial composition, preferably as an antibacterial composition against fish bacterial pathogens.

According to another embodiment, the present invention provides a feed additive for fish farming, comprising the antibacterial composition or the probiotic composition as an active ingredient. In addition to the above active ingredient, the feed additive of the present invention may further comprise an additive such as a known carrier or stabilizer, etc. that is pharmaceutically or sitologically acceptable, or is acceptable as feed. If necessary, the feed additive may comprise various nutrients such as vitamins, amino acids, minerals, etc., antioxidants, antibiotics, antibacterial agents, and other additives. At this time, the feed additive may be in a suitable form such as powder, granule, pellet, suspension, etc.

When the antibacterial composition of the present invention is included in the feed as a feed additive, the composition may be added as it is or mixed with other feed ingredients, and properly used according to a known method. The amount of active ingredients mixed may be properly determined according to use. Since the composition of the present invention is derived from a strain, eco-friendly, and has no particular problem in terms of stability, there is no particular limitation on the amount thereof.

The fish targeted in the present invention preferably includes marine fish such as sea bream, flounder, rockfish, red sea bream, croaker, mullet, sea bass, etc., and land fish such as eel, sweetfish, masu salmon, trout, mandarin fish, etc., and more preferably may be fish such as flounder, turbot, etc., whose taurine production is suppressed, but is not particularly limited thereto.

The feed additive of the present invention is not limited to the above mentioned fish, and can be used for all farmed fish. Preferably, the feed additive may be used for farmed fish which are likely to be infected with a Gram-negative bacterium of *Vibrio anguillarum, V. ichthyoenteri, Aeromonas salmonicida, Edwardsiella tarda, Photobacterium damselae* or a Gram-positive bacterium of *Streptococcus iniae, S. parauberis*.

Also, the feed additive of the present invention may be prepared by a method comprising culturing a *Lactococcus lactis* subspecies *lactis* isolate WFLU-12 in a solid medium; and centrifuging the cultured isolate to harvest a culture. Preferably, the step of culturing may be carried out in an MRS liquid medium at 28° C. for at least 24 hours, preferably 46-50 hours, most preferably 48 hours. Also, the step of harvesting the culture may be carried out by centrifuging the cultured isolate at 3,000 g for 5-30 minutes, preferably 15 minutes. The method for preparing the feed additive may further comprise re-suspending the culture in physiological saline. A feed comprising the feed additive may be prepared by spraying a suspension suspending the culture in physiological saline onto the feed at a concentration of $10^9$ CFU/g to uniformly apply the suspension, and naturally drying the feed.

As described above, since the feed additive is manufactured by a simple method of culturing the isolate and harvesting the culture, the feed additive may be very simply manufactured and may be mass-cultured in a short time. Also, when the feed additive is stored at a temperature of at least 4° C., preferably 4-10° C. after being added to the feed, the number of bacteria in the feed of the isolate of the present invention may be maintained for a certain period of time, and thus it may be stored for a long period of time after being added to the feed. Accordingly, the feed additive may be very useful when practically used as a feed additive in fish farms.

According to another embodiment, the present invention provides a feed for fish farming comprising the feed additive. The form of the feed of the present invention is not particularly limited, and any feed such as powder feed, solid feed, wet pellet feed, dry pellet feed, extruder pellet (EP) feed, raw feed, etc., may be used.

According to another embodiment, the present invention provides a method of promoting the growth of farmed fish comprising feeding the feed to the fish being farmed. At this time, preferably, the feed is supplied in the same amount and feed interval as ordinary feed.

According to another embodiment, the present invention provides a method of preventing infection by pathogens of farmed fish comprising spraying the antibacterial composition to a fish farm. Since the antibacterial composition comprising the *Lactococcus lactis* subspecies *lactis* isolate WFLU-12 of the present invention, a culture thereof, a lysate thereof or an extract thereof as an active ingredient shows an antibacterial activity against fish bacterial pathogens, infection by the pathogens of farmed fish may be prevented by spraying the antibacterial composition to a fish farm so as to inhibit the activity of the bacterial pathogens. The infection with pathogens preferably such as a Gram-negative bacterium of *Vibrio anguillarum, V. ichthyoenteri, Aeromonas salmonicida, Edwardsiella tarda, Photobacterium damselae* or a Gram-positive bacterium of *Streptococcus iniae, S. parauberis* may be prevented by spraying the antibacterial composition of the present invention to the fish farm, but the pathogens are not limited thereto.

MODE FOR CARRYING OUT THE INVENTION

Examples

Example 1—Resistance and Storage Stability of *Lactococcus lactis*

Subspecies *Lactis* Isolate WFLU-12

The *Lactococcus lactis* subspecies *lactis* isolate WFLU-12 of the present invention and isolates not derived from same marine-derived species were tested for their resistance to low temperature, various pH environments and bile acids, and the results are shown in Table 1 below.

TABLE 1

| Species | Growth characteristics [a] | | Bile salt characteristics [a] | |
| --- | --- | --- | --- | --- |
| | Temp (° C.) 10/45 | pH 2/4.4/9.6 | 0.2% 4/24 h | 0.3% 4/24 h |
| Isolates obtained from marine fish gut | | | | |
| Lc. lactis WFLU-12 | +/− | +/+/+ | +/+ | +/− |
| Reference strains | | | | |
| Lc. lactis KCTC 3899 (Earth worm) | +/− | −/+/+ | +/+ | −/− |
| Lc. lactis KCTC 3769 (Milk) | +/− | +/+/+ | +/+ | −/− |
| Lc. lactis KCTC 3768 (Plant) | −/− | −/−/− | +/+ | −/− |
| Lc. lactis KGCM 40699 (Milk) | −/− | −/−/+ | +/+ | −/− |

KCTC: Korean Collection for Type Culture;
KCCM: Korean Culture Center of Microorganisms[a]
+, presence or
−, absence of tolerance As described above, the isolate WFLU-12 grows well at a low temperature and in various pH environments, and in particular has good resistance to bile acids. Also, the fact that the isolate WFLU-12 survives at 10° C. indicates that the isolate may be preserved at a low temperature.

Figure 2:
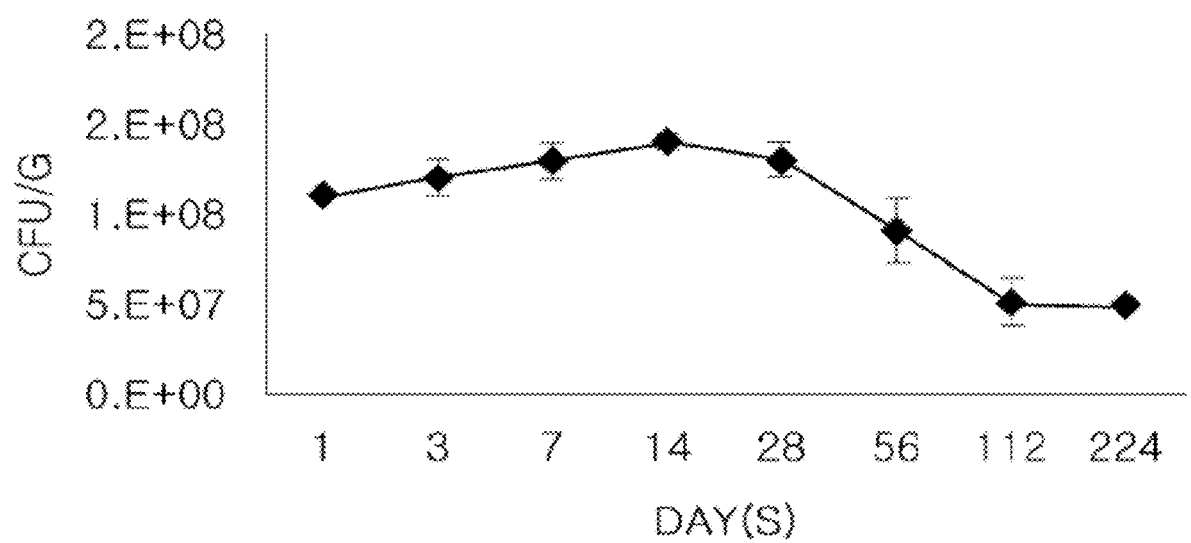
FIG. 2 illustrates long-term survival and stability upon adding the isolate of the present invention to the feed according to an embodiment of the present invention.

In addition, when the feed to which the isolate WFLU-12 of the present invention is added was stored at 4° C., the isolate WFLU-12 survived up to about 8 months, which indicates that the isolate is very capable of long-term survival (FIG. 2). Therefore, when the isolate is stored at 4° C. after being added to the feed, the number of bacteria in the feed of the isolate may be maintained for a certain period of time, and thus it may be stored and used for a long period of time after being added to the feed.

In addition, no clinical symptoms were observed when the isolate WFLU-12 was injected into a fish by intramuscular or intraperitoneal injection. Also, no adverse effects were observed when the isolate was fed to a flounder at a very high concentration (~$10^9$ CFU/g feed) for 8 weeks. In fact, the rate of intake of the fish was very good during the 8 weeks. Therefore, it may be confirmed that the isolate WFLU-12 is a very safe substance which does not adversely affect the fish body.

Example 2—Antibacterial Activity Test

Figure 3:
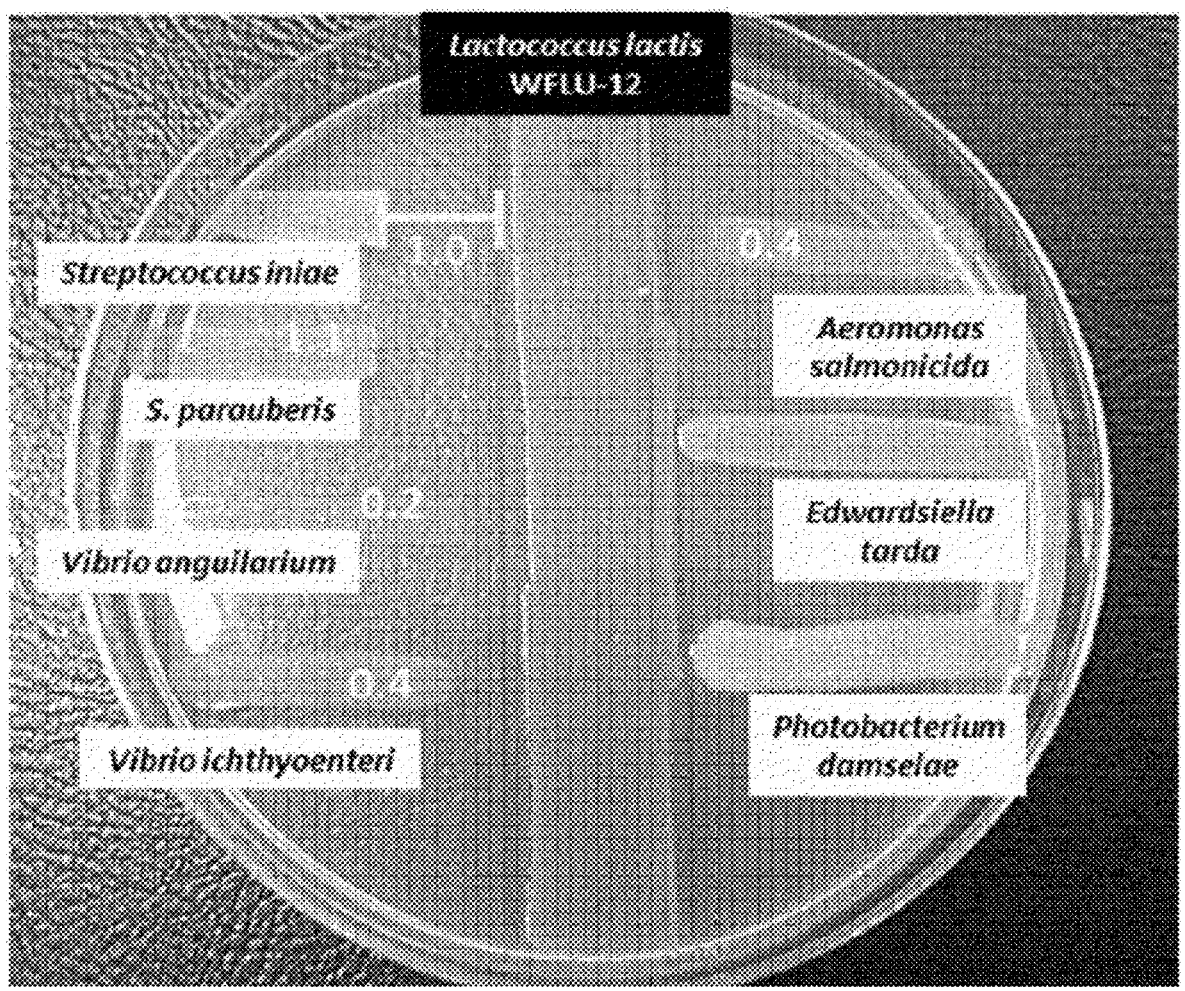
FIG. 3 illustrates an in vitro antibacterial activity test result using a cross-streak method according to an embodiment of the present invention.

The antibacterial activity against fish pathogens was tested using the cross-streak method, and the results are shown in Table 2 and FIG. 3. In FIG. 3, the antibacterial activity was confirmed in *A. salmonicida* (0.4 cm), *S. iniae* (1 cm), *S. parauberis* (1.1 cm), *V. ichthyoenteri* (0.4 cm).

TABLE 2

| Species | Source of isolation | Antimicrobial activity [a] | | | | | | |
| --- | --- | --- | --- | --- | --- | --- | --- | --- |
| | | Aeromonas salmoicida | Edwardsiella tarda | Photobacterium damselae | Streptococcus iniae | Streptococcus parauberis | Vibrio anguillarum | Vibrio ichthyoenteri |
| Isolates obtained from fish gut | | | | | | | | |
| *Lc. lactis* WFLU12 | Olive flounder | ++ | + | − | +++ | +++ | + | + |
| Reference strains | | | | | | | | |
| *Lc. lactis* KCTC 3899 | Earthworm intestine | ++ | + | − | − | − | + | + |
| *Lc. lactis* ATCC 19435 | Milk | + | − | − | − | − | − | − |

TABLE 2-continued

| | | Antimicrobial activity [a] | | | | | | |
|---|---|---|---|---|---|---|---|---|
| Species | Source of isolation | Aeromonas salmoicida | Edwardsiella tarda | Photobacterium damselae | Streptococcus iniae | Streptococcus parauberis | Vibrio anguillarum | Vibrio ichthyoenteri |
| *Lc. lactis | Leaf hopper | + | − | − | − | − | − | − |
| *Lc. lactis ATCC 19257 | Raw milk | − | − | − | − | − | − | − |

KCTC: Korean Collection for Type Culture; ATCC: American Type Culture Collection;
[a] Inhibition zone(mm): ++++ = 16-20 mm; +++ = 11-15 mm; ++ = 6-10 mm; + = 1-5 mm; − = no inhibition
*The results were recorded using both cross-streaking method and agar well diffusion assay.

Also, in Table 2, isolates of same species from different orientations have very weak or no inhibitory effect against fish pathogens, but the isolate WFLU-12 of the present invention showed a broad and strong antibacterial activity against all Gram-negative pathogenic bacteria (*Vibrio anguillarum, V. ichthyoenteri, Aeromonas salmonicida, Edwardsiella tarda, Photobacterium damselae*) and Gram-positive pathogenic bacteria (*Streptococcus iniae, S. parauberis*).

Figure 4:
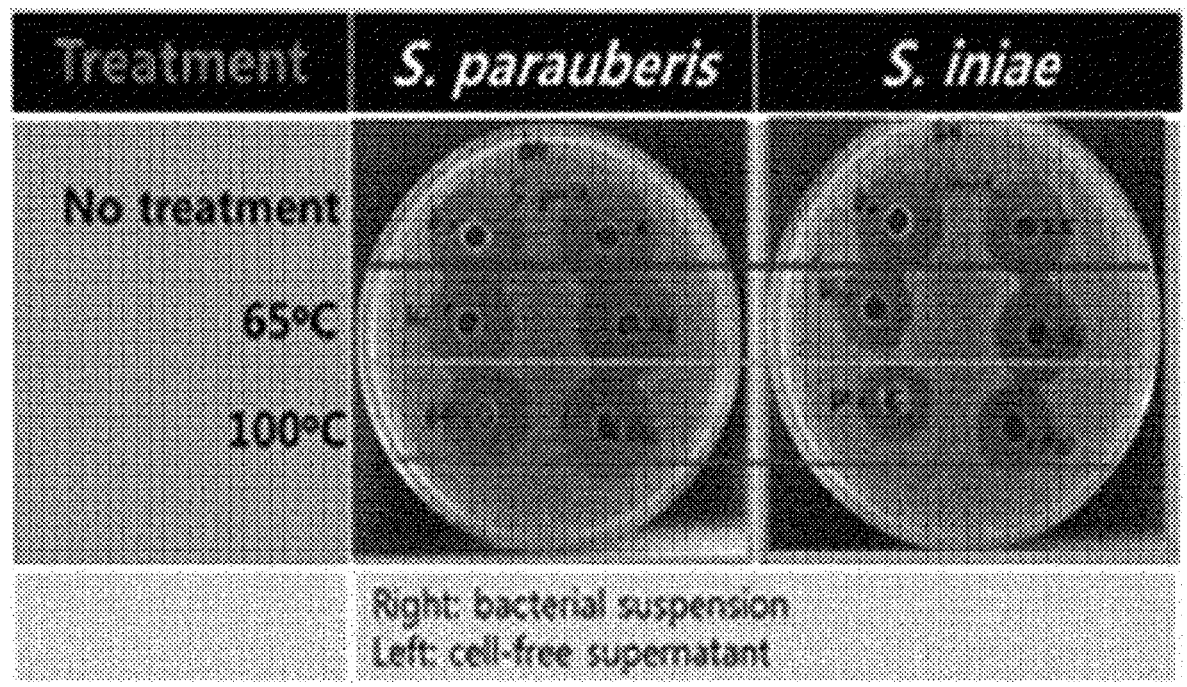
FIG. 4 illustrates the change in antibacterial activity of the heat-treated *Lc. lactis* subsp. *lactis* WFLU-12 against *S. iniae* and *S. parauberis* according to an embodiment of the present invention.

In addition, the substance (supernatant) obtained from the culture medium of the isolate of the present invention was heat-treated to 65° C. and 100° C., and the results are shown in Table 3 and FIG. 4. As a result of heat treatment, inhibitory activity was shown only against *streptococcus*. This suggests that WFLU-12 can produce antibiotics inhibiting pathogens, but heat-resistant bacteriocin exerts antibiotic effects only on Gram-positive bacteria.

TABLE 3

| | No | Heat treated | |
|---|---|---|---|
| Indicator strains | treatment | 650° C. | 1000° C. |
| A. samonicida | + | − | − |
| E. tarda | + | − | − |
| S. iniae | + | + | + |
| S. parauberis | + | + | + |
| V. anguilarium | + | − | − |
| V. ichthyoenteri | + | − | − |
| V. harvey | + | − | − |

+, positive inhibition;
− negative inhibition

Preparation of Feed

A feed comprising the *Lactococcus lactis* subspecies *lactis* isolate WFLU-12 feed additive used in the present invention was prepared through the following steps.

In a solid medium, *Lactococcus lactis* subspecies *lactis* isolate WFLU-12 was cultured in MRS liquid medium at 28° C. for 48 hours. Then, a culture was harvested by centrifugation at 3,000 g for 15 minutes, resuspended in physiological saline, and adjusted to a concentration of $10^9$ CFU/g feed weight, and the suspension was applied by being sprayed onto the feed. Then, the feed was dried naturally.

Example 3—Pathogen Exclusion Activity

The following test was carried out having a flounder fed with a general compound feed as a control group and a flounder fed with a feed to which WFLU-12 probiotic was added as an experimental group (probiotic).

Figure 5:
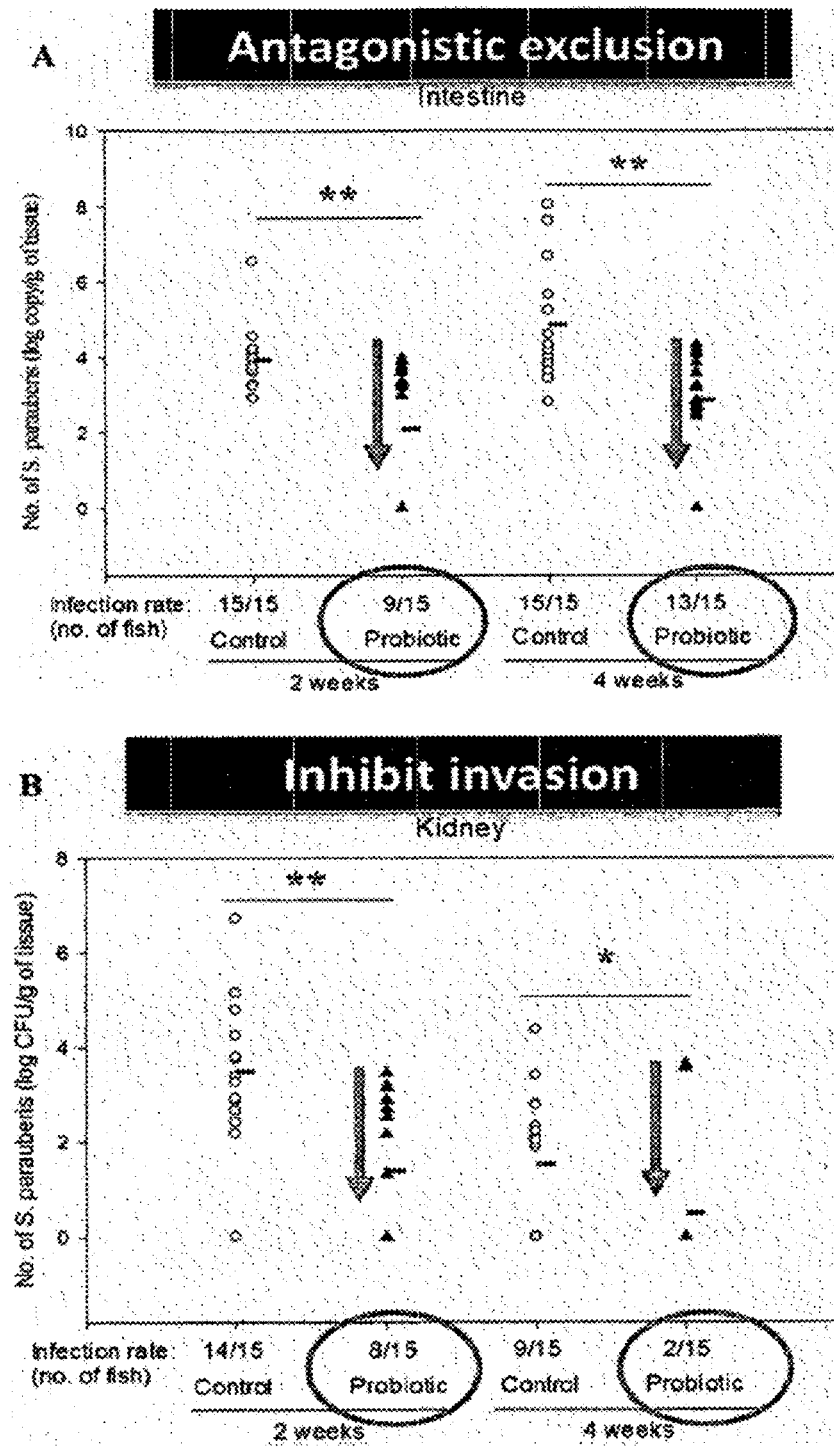
FIG. 5 illustrates the competitive exclusion activity of probiotic isolates in flounder according to an embodiment of the present invention.

After orally infected with *Streptococcus* parauberis, the numbers of bacteria in the intestinal and renal tissues were compared (FIG. 5). The average value of *Streptococcus* parauberis in the intestine and kidney was significantly lower in both week 2 and week 4 of the experimental group as compared with the control group. Therefore, it can be confirmed that the isolate WFLU-12 of the present invention has a function of inhibiting the invasion of streptococcal pathogens. In FIG. 5, the arrows show a significant exclusion of pathogen colonization and invasion in the fish of the experimental group. ((*) and ()) indicate the statistical significance as compared with the control group, which are $p<0.05$ and $p<0.01$, respectively. The same applies to all other graphs of the present invention, and (*) indicates $p<0.001$.)

The beneficial effect of the isolate WFLU-12 in flounder is proven by the natural infection rate of bacteria. As shown in Table 4 below, in a pilot-scale prey test, the infection rate of the experiment group (33%=10/30) was significantly lower than that of the control group (60%=18/30) (Fisher's exact test, $p<0.05$). Mixed infection occurred more frequently in the control group than in the experimental group (experimental group: 6.7%=2/30; control group: 26.7%=8/30). In particular, as for Streptococcal infection disease by *S. parauberis*, 60% was infected in the control group at week 2 (6/10), whereas infection by this bacterium was not detected in the experimental group for the 8 weeks. This result shows that the isolate WFLU-12 of the present invention may provide protection against bacterial pathogens in the intestinal tract.

TABLE 4

| Treatment | No. of infected fish | Pathogen detection (no. of fish) | | | | | |
|---|---|---|---|---|---|---|---|
| | | S. parauberis | P. damselae | V. harveyi | V. ichthyoenteri | Vibrio spp. | Enterococcus sp. |
| Week 2 | | | | | | | |
| Probiotic | 6/10 | — | 4 | — | 3 | — | — |
| Control | 9/10 | 6* | 4 | 1 | — | — | 5 |
| Week 4 | | | | | | | |
| Probiotic | 2/10 | — | — | — | 1 | 2 | — |
| Control | 5/10 | — | 2 | — | 2 | 2 | — |

TABLE 4-continued

| Treatment | No. of infected fish | S. parauberis | P. damselae | V. harveyi | V. ichthyoenteri | Vibrio spp. | Enterococcus sp. |
|---|---|---|---|---|---|---|---|
| Week 8 | | | | | | | |
| Probiotic | 2/10 | — | — | — | — | 2 | — |
| Control | 4/10 | — | 2 | — | — | 2 | — |

—, not detected

Example 4—Increase in Innate Immune Response

Figure 6:
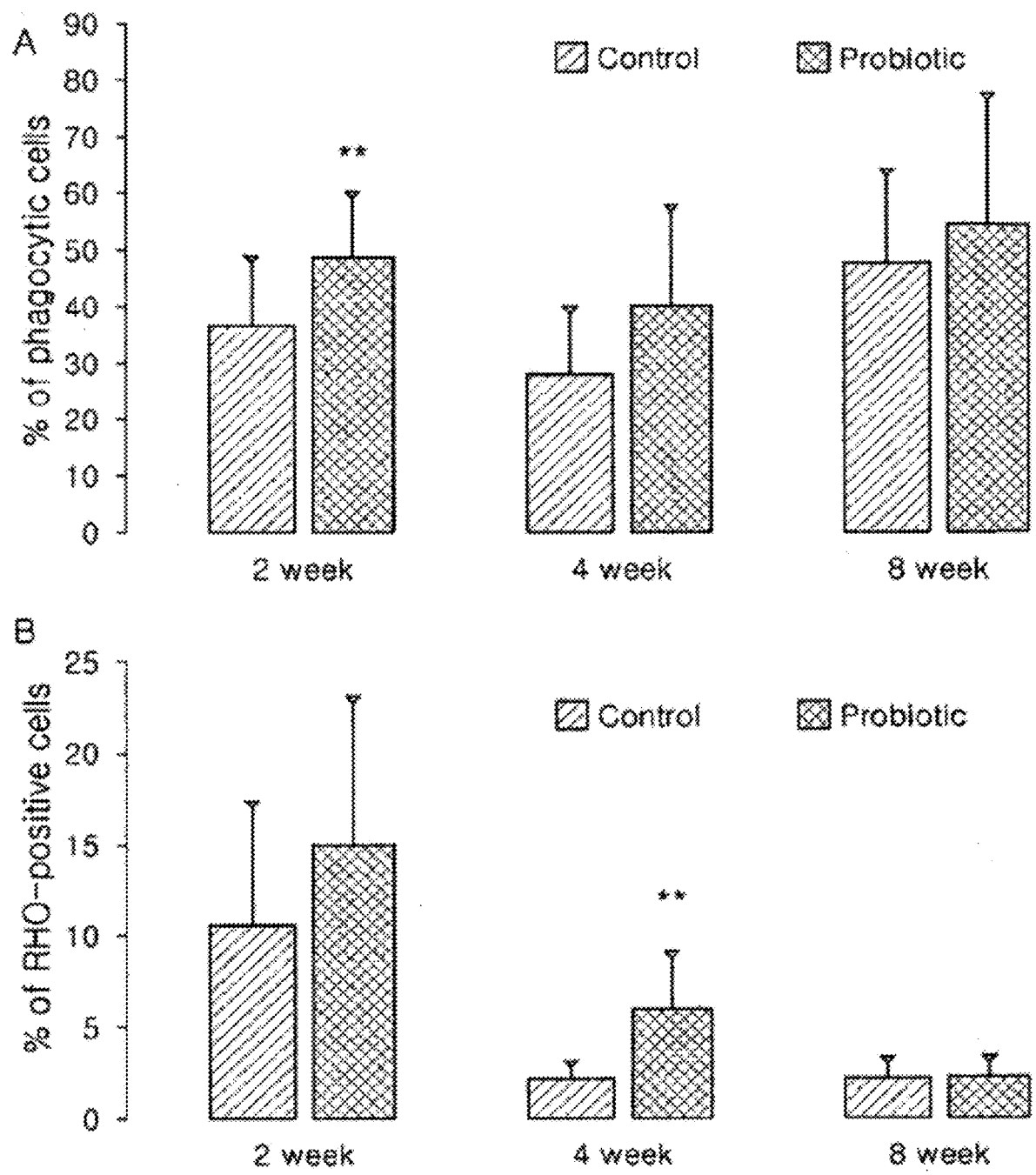
FIG. 6 illustrates the result of comparing the probiotic group and the control group in terms of phagocytotic activity (A) and respiratory burst activity (B) according to an embodiment of the present invention.

FIG. 6 shows the result of measuring phagocytotic activity and respiratory explosive activity by separating the head from the body in the pilot-scale prey test. The experimental group shows a significantly higher activity at week 2 and week 4, respectively. In FIG. 6, each bar represents an average value for 10 fish and shows a standard error.

Figure 7:
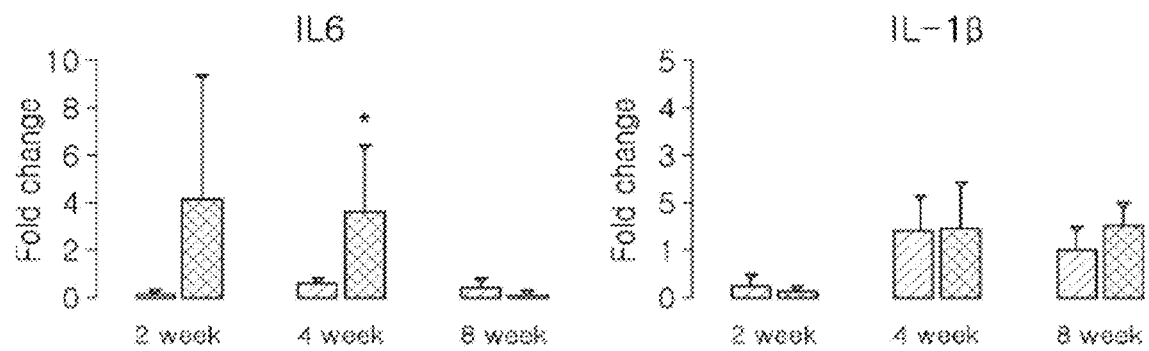
FIG. 7 illustrates the comparison result of pro-inflammatory cytokine expression according to an embodiment of the present invention.
Figure 7:
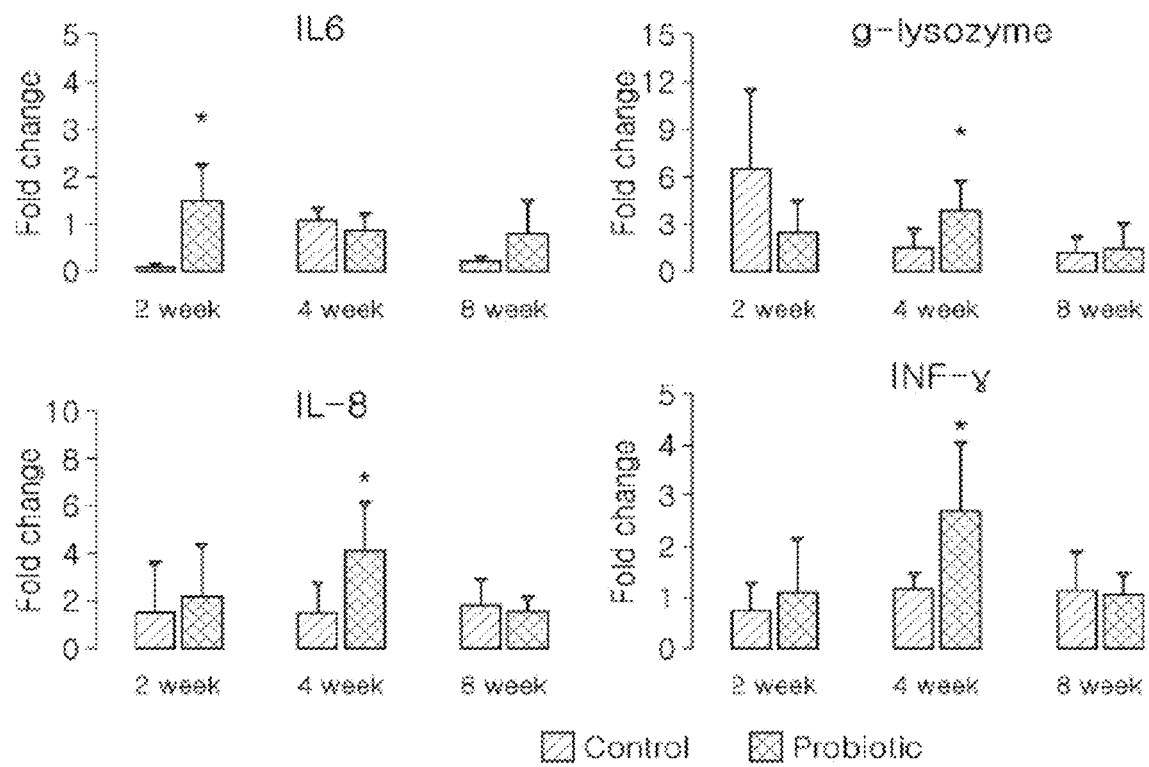

FIG. 7 shows the result of comparing the pro-inflammatory cytokine expression in the experimental group and the control group. From the top, the expression of IL-6 and IL-1β in the intestine, and the expression of IL-6, g-lysozyme, IL-8 and IFN-γ in the kidney were compared, and as a result, it was confirmed that the isolate WFLU-12 induced an increase in the pro-inflammatory cytokine expression and induced an increase in IL-6, IL-8, INF-γ and g-lysozyme in the kidney and an increase in IL-6 in the intestine. Each bar represents an average value for 10 fish and shows a standard error.

Example 5—Enhancing Fish Growth (A) Increase in Body Length and Body Weight

Figure 8:
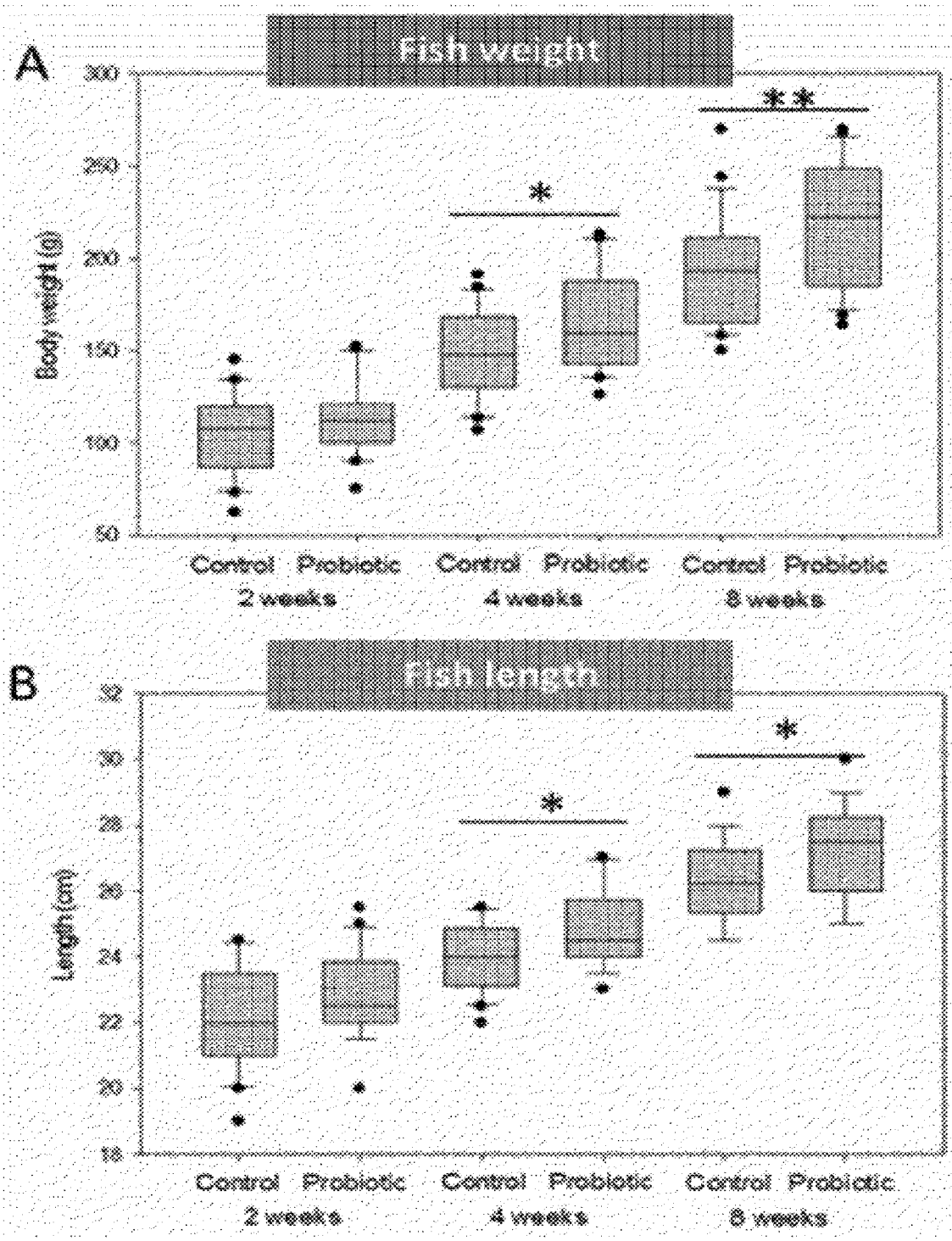
FIG. 8 illustrates the change in body weight (A) and the change in body length (B) according to an embodiment of the present invention.

The growing trend, i.e., body weight change (A) and body length change (B) of the control group and the experimental group ($10^9$ CFU/g) were observed for 8 weeks (~80 g/fish, n=100), and the results are shown in FIG. 8. In FIG. 8, the bars in the graphs represent average values together with standard errors.

There was no significant difference in body weight increase and body length increase in both groups until week 2. However, at week 4, the average body weight of the control group being 147.40±22.47 g, and the average body weight of the experimental group being 164.15±24.73 g, there was a significant difference in average body weight ($p<0.05$), and at week 8, the average body weight of the control group being 192.91±29.31 g, and the average body weight of the experimental group being 217.88±33.36 g, there was a statistically significant difference in average body weight ($p<0.01$) (FIG. 8A). As for change in body length, fish in the experimental group showed a higher growth than the fish in the control group ($p<0.05$). That is, at week 4, fish in the control group grew to be 24.03±0.94 cm, and fish in the experimental group grew to be 24.73±1.18 cm, and at week 8, fish in the control group grew to be 26.36±1.24 cm, and fish in the experimental group grew to be 27.28±1.33 cm, showing a higher growth in the experimental group (FIG. 8B).

(B) High Feed Efficiency and Specific Growth Rate

Figure 9:
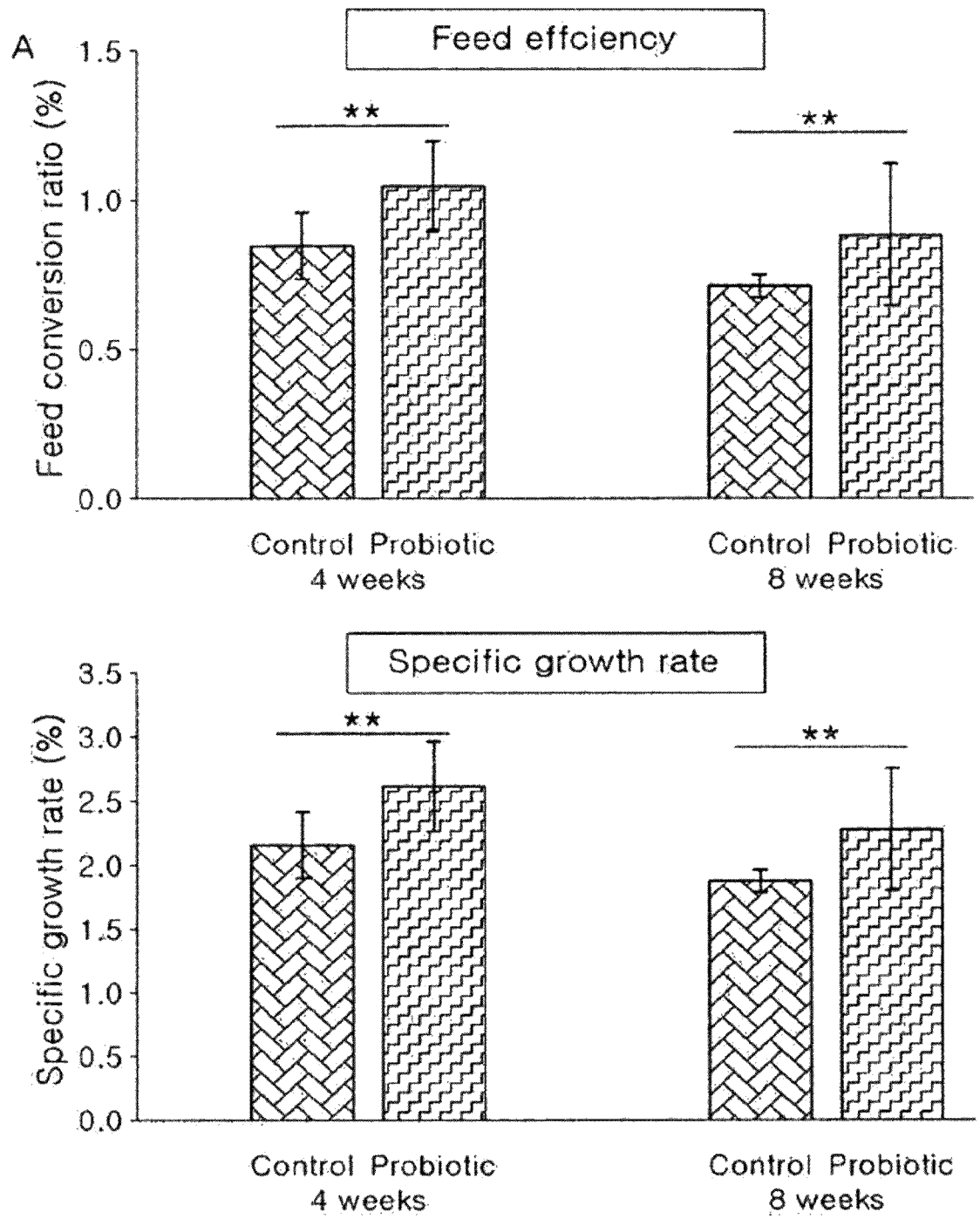
FIG. 9 illustrates the comparison result of feed efficiency and specific growth rate (SGR) according to an embodiment of the present invention.

As a result of observing the feed conversion rate and specific growth rate for 8 weeks, there was a significant difference between the control group and the experimental group ($p<0.01$). The results are shown in FIG. 9. In FIG. 9, the bars in the graphs represent average values together with standard errors. The feed efficiency was 0.85±0.11, 1.04±0.04 at week 4, and 0.71±0.15, 0.89±0.23 at week 8 (FIG. 9, top). The specific growth rates of the control group and the experimental group were 2.15±0.24 and 2.58±0.08, respectively, at week 4, and 1.87±0.30 and 2.29±0.44, respectively, at week 8 (FIG. 9, bottom). These results indicate that the addition of probiotic makes a positive contribution to enhancing fish growth and feed efficiency.

(C) Confirming Metabolite (Nutrient) in Intestinal Tract of Fish

The metabolites of the control group and the experimental group were compared assuming that the difference in fish growth between the control group and the experimental group is related to the fact that different patterns of gut microbiomes would be associated with beneficial metabolites of intestinal substances, total proteins, enzyme activity promotion, etc.

Figure 10:
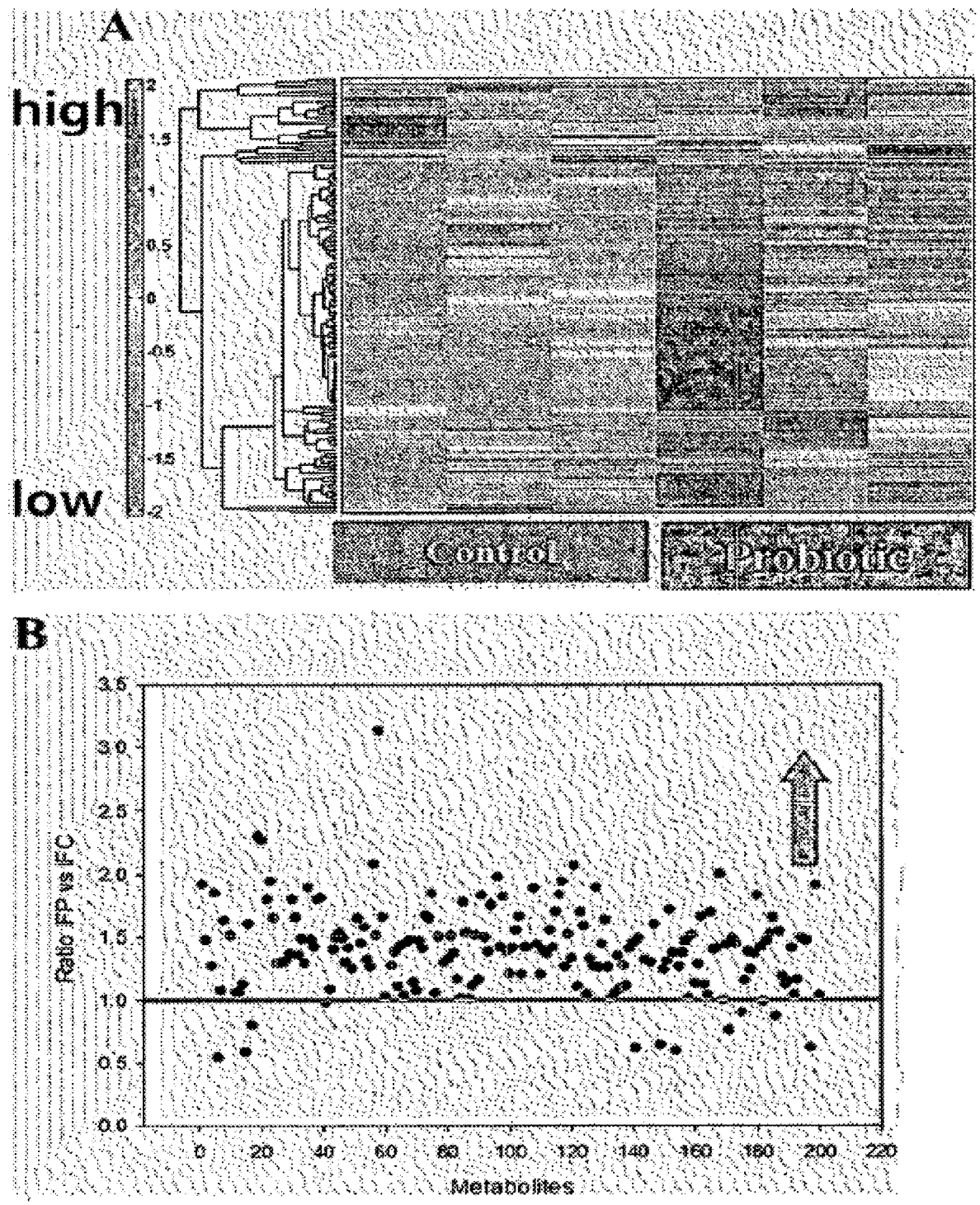
FIG. 10 illustrates enhancement of metabolites according to an embodiment of the present invention.

FIG. 10A shows a metabolite pattern (A) represented by hierarchical clustering, with red and green representing metabolites of high concentration and low concentration, respectively. FIG. 10B shows the ratio of the experimental group vs the control group (IFP vs IFC) calculated by using the average of the detected values. The red arrow indicates that metabolites are enhanced in the experimental group.

As a result of analyzing the metabolites, FIG. 10A shows that lipid metabolism-related substances and major carbon metabolic intermediates were more prevalently expressed in the experimental group. In addition, the scatter plot in FIG. 10B shows that most of the metabolites in the intestines are expressed higher in the experimental group than in the control group. This result suggests that specific metabolites are involved in relation between probiotic bacteria in the intestines and fish growth.

(D) Maintaining Homeostasis of Metabolites Circulating in Fish Body

Figure 11:
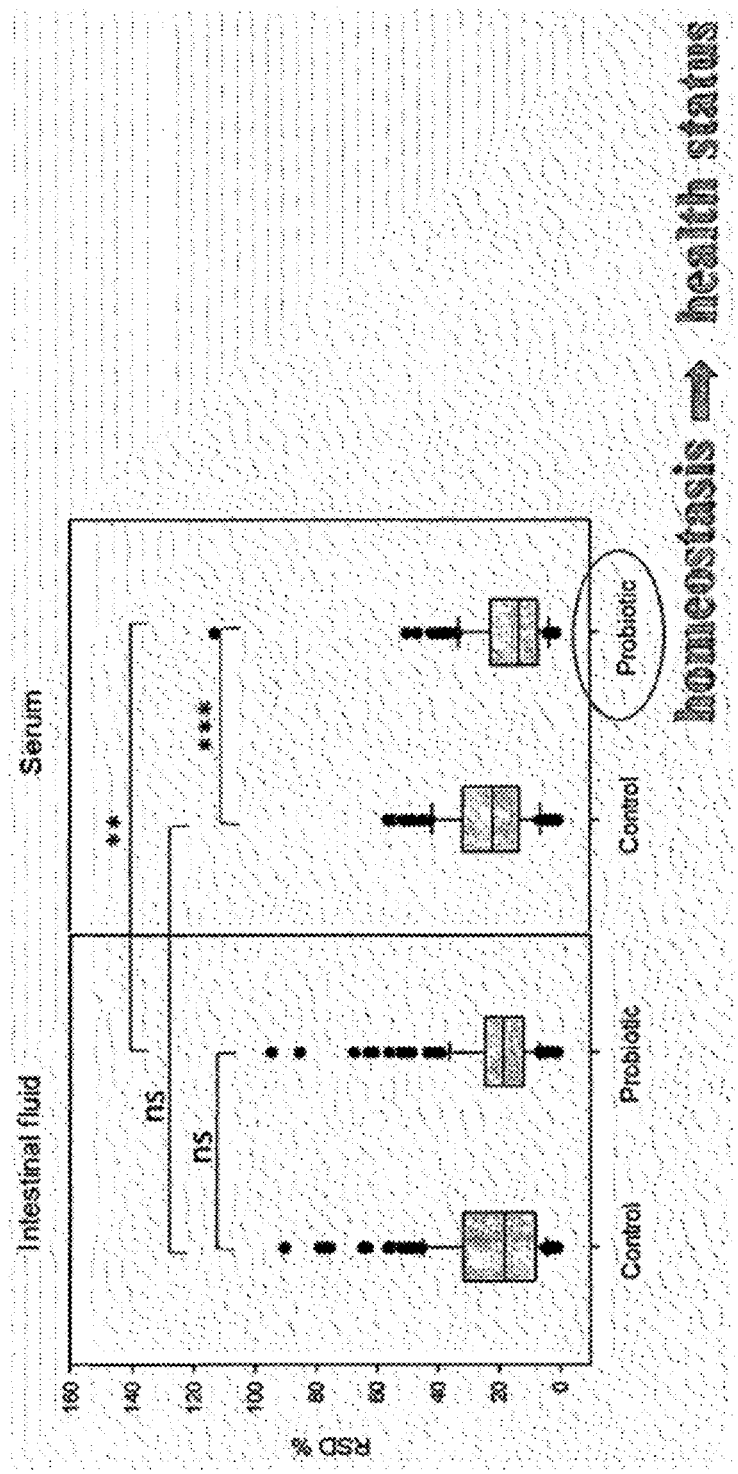
FIG. 11 illustrates the relative standard deviation (RSD %) of all metabolites detected in intestinal fluid and serum according to an embodiment of the present invention.

In order to confirm the effect of maintaining homeostasis of metabolites circulating in fish body, a graph of box plots showing the relative standard deviation (RSD %) of all metabolites detected in the intestinal fluid and serum was prepared and presented in FIG. 11.

The difference in relative standard deviation (RSD) values of the metabolites indicate the difference in individual metabolites, and the metabolites in serum are affected by the metabolites produced by intestinal bacteria (Matsumoto et al., 2013; Front Syst Neurosci. 2013 Apr. 23; 7:9). The RSD values of intestinal substances were similar in both groups in terms of variability of metabolites ($p=0.348$), but the RSD values of serum were the most stable in the experimental group ($p<0.001$). That is, serum in the experimental group generally showed good homeostasis, whereas some fish in the control group showed relative unevenness (metabolites synthesized in host tissues). Just like the addition of probiotic to feed could gradually enhance the digestion capacity of the flounder over a period of weeks, the high homeostasis could be attributed to the appropriate nutritional status required by the fish. The isolate WFLU-12 of the present invention is considered to help maintain a strong homeostasis of metabolites circulating throughout the body.

Example 6—Increase in Sulfur-Containing Amino Acid Level in Fish Body

Figure 12:
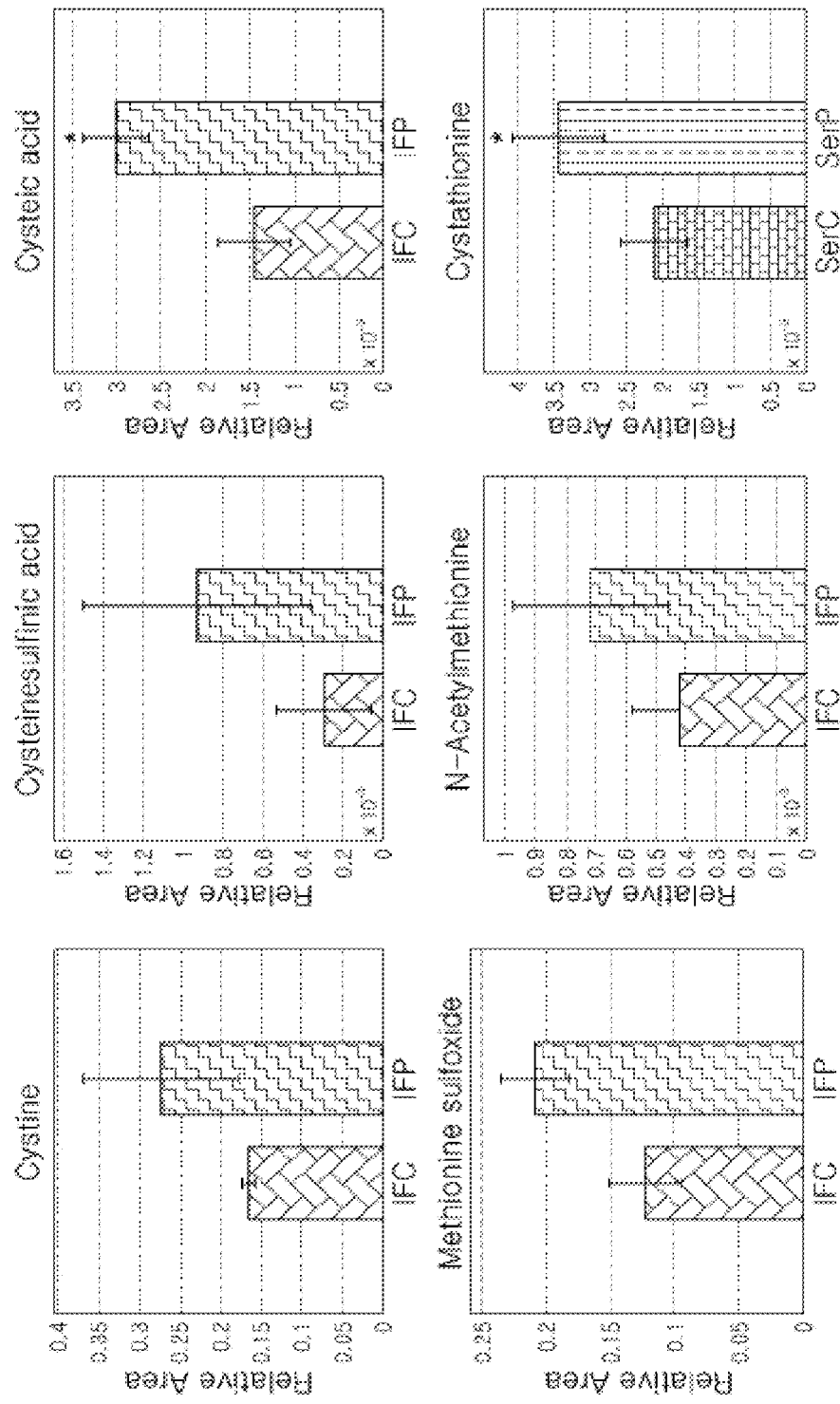
FIG. 12 illustrates the comparison result of sulfur-containing amino acid levels in fish bodies according to an embodiment of the present invention.

The degree of increase in sulfur-containing amino acid level in the fish body was measured in the control group and the experimental group, and the results are shown in FIG. 12. The blue bar graph (intestine) and the yellow bar graph (serum) represent the control group, and the red bar graph (intestine) and the green bar graph (serum) represent the experimental group.

Like other amino acids, sulfur-containing amino acids affect protein metabolism. They are components of tissue protein, and lack of these amino acids decreases protein synthesis. It has been reported that supplementing methionine has an effect on the muscle growth of chickens, and as a result of adding methionine to methionine-deficient feed (with other balanced amino acids added), protein synthesis and attachment increased in skeletal muscles.

As a result of comparing N-acetyl-methionine, which is a precursor of sulfur-containing amino acids in fish, in the control group and the experimental group, the present invention shows that N-acetyl-methionine increased 1.7 times in the intestine of the experimental group. Other sulfur-containing amino acid derivatives such as methionine sulfoxide ($p<0.05$), cysteine (1.6-fold increase), cysteine sulfonic acid (3.1-fold increase), cysteic acid ($p<0.05$) were expressed significantly higher in the experimental group than in the control group. This increase in sulfur-containing amino acid level leads to a significant increase in cystathionin ($p<0.05$) in circulating metabolites in which probiotics are involved in the synthesis of sulfur-containing amino acids, and to an increase of protein synthesis in fish organs.

In addition to the above, cystathionin increased in fish tissues (muscles) fed with cystine-added feed, and the growth also enhanced as compared with the control group (Park et al., 2002; Fisheries science Vol. 68 (2002) No. 4 P 824-829). Therefore, sulfur-containing amino acid precursors, especially cystathionin, act as an important marker for fish growth. They also play an important role in taurine biosynthesis, and in particular since cysteic acid produces taurine successively after enhancing the secretion of taurocholic acid (bile acid), cysteic acid may be used as the sole source of taurine formation.

Example 7—Increase in Taurine in Fish Intestines

Figure 13:
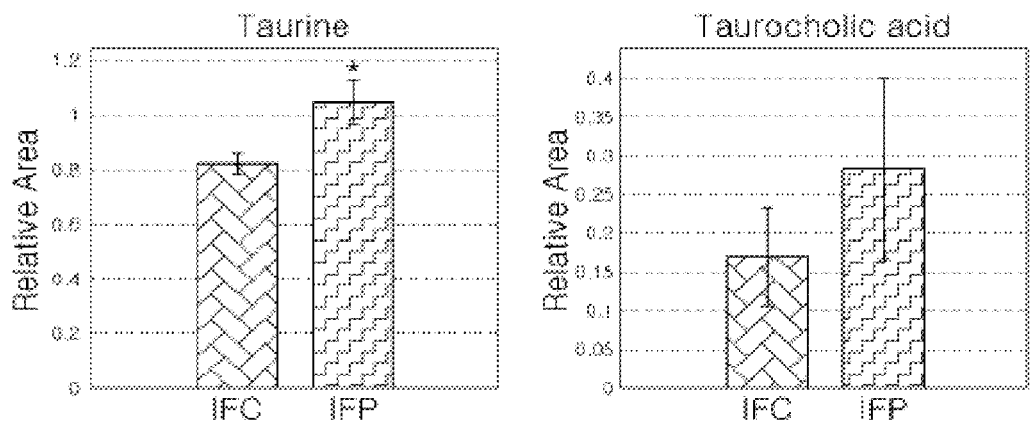
FIG. 13 illustrates the comparison result of an increase in taurine and bile acid levels in the intestine of a fish according to an embodiment of the present invention.

The degree of increase in taurine and bile acid in fish intestines was measured in the control group and the experimental group, and the results are shown in FIG. 13. The blue bar graph (intestine) represents the control group, and the red bar graph (intestine) represents the experimental group.

Taurine (2-amino ethanesulfonic acid) is a sulfur-containing amino acid that participates in a wide variety of physiological processes, in particular in the production of bile acid complexes, osmotic pressure regulation, calcium homeostasis, skeletal muscle, nerves and retinal function in vertebrate animals. In vivo synthesis of taurine in fish varies widely depending on species, and in particular it is well known that the synthesis of taurine in flounder and turbot is limited. Taurine is conjugated with bile acids to produce taurocholic acid, which accounts for 95% or more of the total bile acid complex in flounder. Therefore, taurine is a very essential nutrient that affects the growth of young flounders.

The addition of sulfur-containing amino acids to the feed did not promote the biosynthesis of taurine in the flounder, but it appears that the addition of the isolate WFLU-12 of the present research to the feed controls the expression of the related amino acids in the intestines of the flounder. The isolate of the present invention contributes to enhancing the level of intermediate amino acids such as cysteic acid (CA), cysteine sulfinic acid (CSA), etc., in the intestines of the fish, thereby increasing the level of taurine (FIG. 13). Therefore, the addition of the isolate of the present invention may enhance fish growth through the efficiency of fat digestion of fish, and further save the costs for adding taurine.

Example 8—Enhancing Citrulline Level in Fish Body

Figure 14:
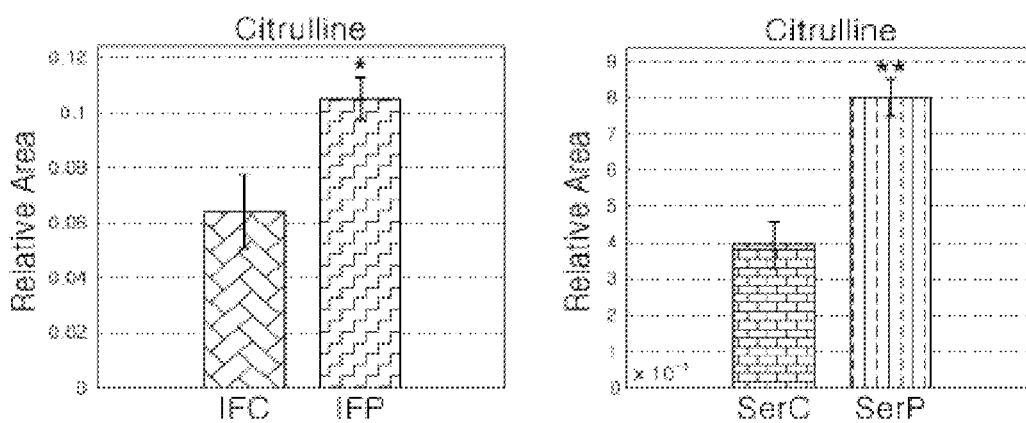
FIG. 14 illustrates the comparison result of an increase in citrulline level in intestine and serum according to an embodiment of the present invention.

The degree of increase in citrulline in the intestine and serum was measured in the control group and the experimental group, and the results are shown in FIG. 14. The blue bar graph (intestine) and the yellow bar graph (serum) represent the control group, and the red bar graph (intestine) and the green bar graph (serum) represent the experimental group.

Fish requires a high level of arginine in the feed because arginine is rich in protein (as a peptide bound to amino acids) and tissue fluid (phosphoarginine), which mainly stores ATP. Ureogenic teleost may convert citrulline to arginine in the liver by arginosuccinate synthase and lyase (Mommsen et al., 2001). However, it is unknown whether there is a net synthesis of citrulline or arginine in the liver of aquatic animals.

The level of citrulline increased in the intestines and circulating blood (serum) of the experimental group in the present invention (FIG. 14). Since the elevated level of circulating citrulline may be used for endogenous synthesis of arginine in almost all types of cell (adipocytes, endothelial cell, enterocyte, macrophage, neurons, myocytes) (Wu and Morris, 1998), it may contribute to the efficiency of using nutrients and then to the fish growth. The inducement of citrulline synthesis by the isolate of the present invention may inhibit citrulline synthesis in glutamine and glutamate, which may spare the use of glutamine and glutamate for other metabolic pathways or activities. (For example, glutamine may be converted to glutamate, and glutamate may directly enhance growth hormone secretion.)

Example 9—Enhancing Vitamin Level in Fish Intestines

Figure 15:
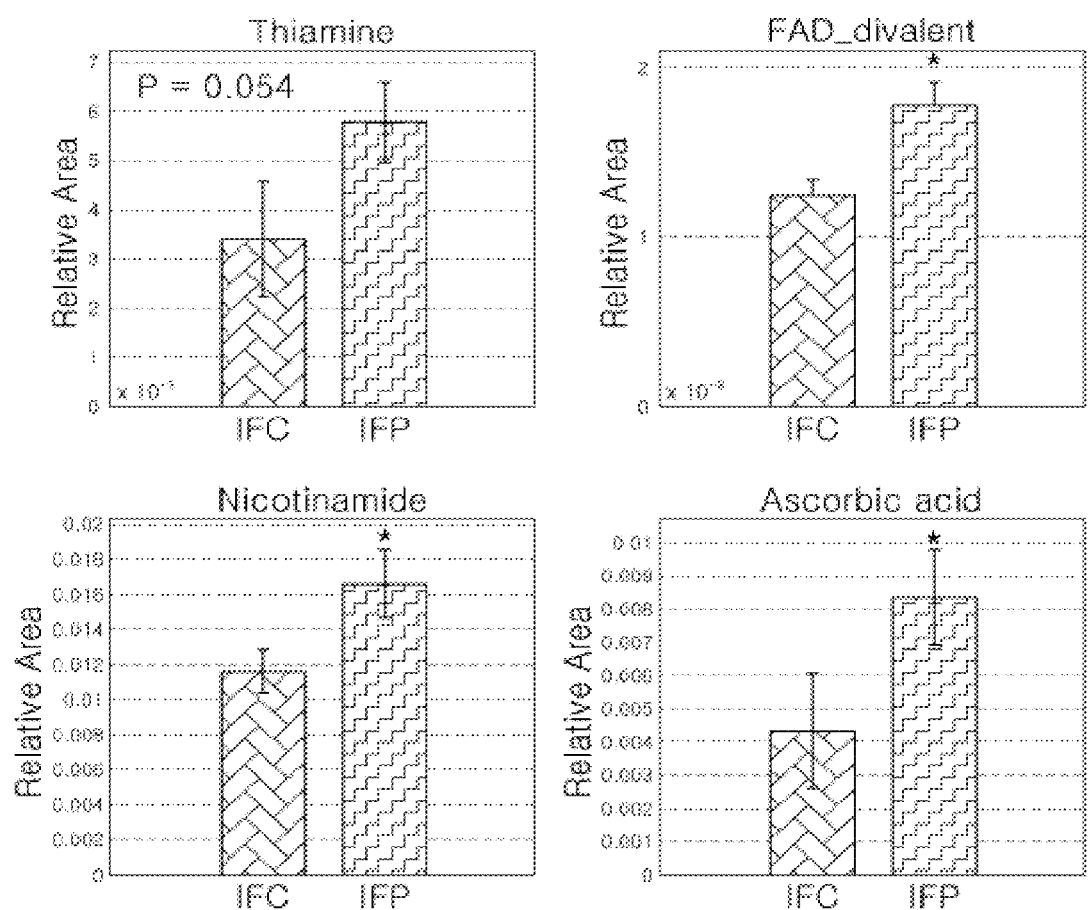
FIG. 15 illustrates graphs comparing the biosynthesis of vitamin B1 (Thiamine), B2 (FAD_divalent), B3 (Nicotinamide), and C (Ascorbic acid) according to an embodiment of the present invention.

The degree of biosynthesis of vitamin B1 (Thiamine), B2 (FAD_divalent), B3 (Nicotinamide), and C (Ascorbic acid) was measured in the control group and the experimental group, and the results are shown in FIG. 15. The blue bar graph (intestine) represents the control group, and the red bar graph (intestine) represents the experimental group.

Vitamins are organic compounds which are essential nutrients for fish growth and health. Some vitamins are not synthesized in the fish body, and must be ingested through a food source. It has been confirmed that fish fed by adding the isolate WFLU-12 of the present invention showed an increase in the level of vitamin B and vitamin C (ascorbic acid) (FIG. 15).

What is claimed is:

1. A method of providing antibacterial activity to a fish comprising:
   administering to the fish a probiotic composition comprising the *Lactococcus lactis* subspecies *lactis* isolate WFLU-12 deposited under the accession number KCTC13180BP or a culture thereof.

2. The method of claim 1, wherein the isolate shows resistance to a temperature of at least 4° C., a pH of 2 to 10, and/or a bile acid.

3. The method of claim 1, wherein the method provides antibacterial activity against a Gram-negative bacterium of *Vibrio anguillarum, V. ichthyoenteri, Aeromonas salmonicida,* or *Edwardsiella tarda,* or a Gram-positive bacterium of *Streptococcus iniae,* or *S. parauberis.*

4. A method of providing to a fish at least one effect selected from enhancing innate immune response, increasing body weight, increasing body length, enhancing lipid metabolism-related substances and carbon metabolic intermediates, maintaining body circulating metabolites, enhancing body citrulline level, maintaining homeostasis of metabolites, increasing the expression level of N-acetyl methionine, methionine sulfoxide, cysteine sulfonic acid, cysteic acid, increasing the level of taurine and bile acid in intestine, and enhancing the level of B1, B2, B3 and C vitamins in the fish comprising administering to the fish a probiotic composition comprising the *Lactococcus lactis* subspecies *lactis* isolate WFLU-12 deposited under the accession number KCTC13180BP or a culture thereof, wherein the increase or the enhancement is when compared to a corresponding fish not administered with the probiotic composition.

5. A method of promoting growth of a fish comprising administering to the fish an antibacterial composition comprising the *Lactococcus lactis* subspecies *lactis* isolate WFLU-12 deposited under the accession number KCTC13180BP or a culture thereof.

6. The method of claim 5, wherein the antibacterial composition is a feed additive for fish farming.

7. A method of inhibiting the infecting activity of a bacterial pathogen in a fish comprising spraying the fish with an antibacterial composition comprising the *Lactococcus lactis* subspecies *lactis* isolate WFLU-12 deposited under the accession number KCTC13180BP or a culture thereof.

* * * * *